(12) United States Patent
Wen et al.

(10) Patent No.: US 10,702,519 B2
(45) Date of Patent: Jul. 7, 2020

(54) USE OF METHOXATIN, DERIVATIVE AND/OR SALT THEREOF IN SJOGREN'S SYNDROME AND PHARMACEUTICAL COMPOSITION

(71) Applicant: NANJING SHUPENG LIFESCIENCE CO., LTD, Nanjing, Jiangsu (CN)

(72) Inventors: Chuanjun Wen, Jiangsu (CN); Fenyong Sun, Jiangsu (CN)

(73) Assignee: NANJING SHUPENG LIFESCIENCE CO., LTD, Nanjing, Jiangsu (CN)

( * ) Notice: Subject to any disclaimer, the term of this patent is extended or adjusted under 35 U.S.C. 154(b) by 0 days.

(21) Appl. No.: 16/074,449

(22) PCT Filed: Jan. 22, 2017

(86) PCT No.: PCT/CN2017/072130
§ 371 (c)(1),
(2) Date: Aug. 1, 2018

(87) PCT Pub. No.: WO2017/133523
PCT Pub. Date: Aug. 10, 2017

(65) Prior Publication Data
US 2019/0030024 A1 Jan. 31, 2019

(30) Foreign Application Priority Data
Feb. 4, 2016 (CN) .......................... 2016 1 0080478

(51) Int. Cl.
*A61K 31/4745* (2006.01)
*A61P 27/02* (2006.01)
*A61P 1/02* (2006.01)
*A61K 45/06* (2006.01)
*A61K 31/593* (2006.01)
*A61P 37/02* (2006.01)

(52) U.S. Cl.
CPC ........ *A61K 31/4745* (2013.01); *A61K 31/593* (2013.01); *A61K 45/06* (2013.01); *A61P 1/02* (2018.01); *A61P 27/02* (2018.01); *A61P 37/02* (2018.01)

(58) Field of Classification Search
CPC .............. A61K 31/593; A61K 2300/00; A61K 31/4745; A61K 45/06; A61P 1/02; A61P 27/02; A61P 37/02
See application file for complete search history.

(56) References Cited

U.S. PATENT DOCUMENTS

| | | | | |
|---|---|---|---|---|
| 5,460,819 A | * | 10/1995 | Gallop ................... | A61K 31/47 514/292 |
| 2015/0056176 A1 | * | 2/2015 | Jankowitz ............ | A61K 31/352 424/94.1 |
| 2016/0000794 A1 | * | 1/2016 | Chiorini ............... | A61K 31/519 514/252.16 |

OTHER PUBLICATIONS

Rucker et al. (Alternative Medicine Review, 14, 3, 2009) (Year: 2009).*
Karteek et al. (Int J of Pharmaceutical Sciences Review and Research, 5, 1, 2010, p. 93-99). (Year: 2010).*
Tincani (BMC Medicine, 2013, p. 1-17). (Year: 2013).*

* cited by examiner

*Primary Examiner* — Umamaheswari Remachandran
(74) *Attorney, Agent, or Firm* — IPro, PLLC

(57) ABSTRACT

The present invention relates to use of pyrroloquinoline quinone (PQQ), a derivative and/or a salt thereof of formula (I) in the preparation of a drug for treating and/or preventing primary Sjogren's syndrome, secondary Sjogren's syndrome as well as dry mouth, dry eye and multiple system damages accompanied by the involvement of other exocrine glands and other organs outside the glands caused by Sjogren's syndrome. In formula (I), R1, R2 and R3 being same or different, each independently representing lower alkyl, lower alkenyl, lower alkynyl, aralkyl, alkaryl, phenyl, a hydrogen atom, sodium atom or a potassium atom; and PQQ or pharmaceutical combinations of PQQ combined with active vitamin D, NAC, resveratrol, epigallocatechin gallate, curcumin, anthocyanin, vitamin E, vitamin C, or vitamin D and the like. The drug and the pharmaceutical combinations can treat Sjogren's syndrome and associated diseases which are derivative of Sjogren's syndrome. The present invention can remove excess oxygen radicals in the body, inhibit NF-kB activation caused by oxidative stress, and inhibit autoimmunity, thereby reducing the inflammatory response of Sjogren's syndrome.

8 Claims, 2 Drawing Sheets

USE OF METHOXATIN, DERIVATIVE AND/OR SALT THEREOF IN SJOGREN'S SYNDROME AND PHARMACEUTICAL COMPOSITION

TECHNICAL FIELD

The present invention relates to the use and pharmaceutical composition of pyrroloquinoline quinone (PQQ), its derivative and/or salt in the treatment and/or prevention of Sjogren's syndrome (SS), in particularly to use of pyrroloquinoline quinone (PQQ), a derivative and/or a salt thereof in the preparation of a medication for treating and/or preventing primary Sjogren's syndrome, secondary Sjogren's syndrome as well as dry mouth, dry eye and multiple system damages accompanied by the involvement of other exocrine glands and other organs outside the glands caused by Sjogren's syndrome.

BACKGROUND ART

Sjogren's syndrome is a chronic inflammatory autoimmune disease that mainly involves exocrine glands. Its inflammatory response is mainly manifested in epithelial cells of exocrine glands. Clinically, in addition to the impaired function of salivary glands and lacrimal glands, i.e., dry mouth and dry eyes, there are other exocrine glands and other organs outside the gland and the symptoms of multiple system damage. The patient's serum contains multiple autoantibodies and hyperimmune globulins. The disease is divided into primary and secondary types. Primary Sjogren's syndrome is a global disease with a prevalence of 0.3% to 0.7% in the Chinese population. More than 90% of the patients is female, the ratio of male to female is 1:9 to 1:20, and the age of onset is mostly 40-50 years old. Since the earliest description of Sjogren's syndrome at the end of the 19th century, the research history has been more than a hundred years. Although its pathogenesis has not yet been fully elucidated, some progress has been made since the 1990s. With the development of immunology and molecular biology techniques, the pathogenesis of SS has been studied and the etiology may be related to factors such as heredity, immunity, endocrinology, and viral infection. At present, consensus has been basically reached. Most scholars believe that SS has genetic susceptibility. On this basis, local non-specific inflammation induces the expression of cytokines IFN-γ and TNF-α, triggering a series of immune responses (Ann Rheum Dis, 2003), 62(4):359-62. Clin Rev Allergy Immunol, 2007, 32(3):252-64). Due to the disorder of the immune regulation mechanism, the inflammation is persistently chronic and damages the exocrine glands. Therefore, the pathological changes are mainly the infiltration of lymphocytes and plasma cells into the glandular tissue and cause progressive destruction, resulting in reduced secretion of saliva and tears, and in turn the dry mouth and eyes symptom.

There is no safe and effective treatment for this disease at present. Some measures are mainly taken to improve symptoms, control and delay the progress of tissue damage caused by the immune response and secondary infections. Non-steroidal anti-inflammatory drugs (NSAIDS) are mainly used for the treatment of SS muscles, joint pain, mild serositis and fever and other symptoms, generally have a quicker effect and are effective for several days after administration. However, these treatments are limited to relieve symptoms. The side effects include digestive tract reactions (even bleeding), kidney damage, and myelosuppression. They can also cause liver damage, occasional skin rashes, cytopenia, or pancreatitis. When patients with Sjogren's syndrome have visceral multiple system damage, such as nervous system, blood system, severe interstitial lung disease, vasculitis, hepatic damage, myositis, etc., it is generally necessary to use glucocorticoids for treatment. In critical condition, hormone shock treatment can be used. It should be noted that the use of long-term glucocorticoids can produce the following side effects, such as: iatrogenic adrenocortical hyperactivity, induction and aggravation of infection, induction and aggravation of peptic ulcer, osteoporosis, aseptic bone necrosis. For the patient with rapid progress of the disease, can be administrated in combination with immunosuppressive agents, such as cyclophosphamide, azathioprine and so on.

Although the research history of SS has exceeded 100 years, its etiology and pathogenesis remain unclear. Immunity, genetics, environment, infection, abnormal neuromodulation and other factors may be related to the onset of SS. Studies have shown (Journal of Autoimmunity, 2001, 17:141-153) that there is an extensive and close relationship between cytokines and SS, which plays an important role in the pathogenesis of SS. For example, interferon can both inhibit the growth and differentiation of salivary gland epithelial cells (SGEC) and induce SGEC isolation and apoptosis (J. Immunol, 2000, 164:1277-1285). Tumor necrosis factor (TNF-α) promotes the lysis of glandular cells and alters the adhesion properties of endothelial cells (Adv Exp Med Biol, 1998, 438:909-915). Interleukins regulate cell growth and differentiation in SS exocrine tissue lesions, affect the behavior and characteristics of many cells, participate in inflammatory reactions, and modulate immune responses (Arthritis Rheum, 1997, 40: 987-990). Fox et al. (Cur Opi Rheum, 2000, 12:391-398) found that the levels of IL-1α,6 and TNF-α mRNA produced by SS patient's SGEC are 40-fold higher than those of normal SGEC. The levels of IL-1β, IL-6, IL-10, TNF-α and IFN-γ in salivary glands of SS patients were increased, which can be detected by ELISA (Lab Invest. 1999. 12:1719-1726). Therefore, cytokine-mediated inflammation is an important pathogenesis of SS.

Nuclear factor-κB (NF-κB) is a DNA-binding protein that regulates gene expression. It regulates the expression of many important cytokines, adhesion molecules, and chemokine genes, and participates in various physiological and pathological processes of the body, the most important of which are immune and inflammatory reactions. NF-κB has been shown to be a very important type of transcription factor that is ubiquitous in the course of inflammation and immune response. NF-κB is a rapidly-reacting transcription factor and play a role through the expression of inflammatory mediators (IL-1β, IL-6, IL-10, TNF-α, etc.), adhesion molecules, and enzymes in an inflammatory reaction. In the course of inflammation, NF-κB is involved in the activation of macrophages and leukocytes, and controls the gene expression of many cytokines, inflammatory protein and proinflammatory cytokines. Loss of control in this regulatory process will lead to amplification of the inflammatory response and tissue damage. Studies have shown (Arthritis Res Ther. 2012 Mar. 14; 14(2):R64) that the activation of toll-like receptor 2 (TLR 2) can induce IL-23/IL-17 expression through NF-κB, which process is closely related to the formation of SS. Lisi Si et al. also found that a decrease in the expression of nuclear factor κB inhibitor α (IκBα) can upregulate the NF-κB pathway and increase the production of SS-related cytokines and inflammation, leading to the occurrence of SS (Lisi et al., Pathology. 2012 October; 44(6):557-61).

Oxidative stress (OS) refers to the imbalance between oxidation and antioxidation in the body. Excessive production of highly reactive molecules such as reactive oxygen species (ROS) and reactive nitrogen radicals (RNS) results in the oxidation exceeding oxide removal, leading to neutrophil inflammatory infiltration and tissue damage. ROS includes superoxide anion, hydroxyl radical and hydrogen peroxide; RNS includes nitric oxide, nitrogen dioxide and peroxynitrite. Representative biomarkers of oxidative stress are 8-hydroxydeoxyguanosine (8-OHdG), thioredoxin (TRX).

8-OHdG is a sensitive marker of oxidative stress DNA damage. It is reported that 8-OHdG was found to increase in the saliva of SS patients but not in other patients with salivary gland dysfunction and normal individuals (Ryo et al., Pathobiology. 2006; 73(5):252-60). In SS patients, both protein oxidation markers PC (protein carbonyl) and APOO (Advanced Oxidation Protein Product) were increased (Free Radic Res. 2012 February; 46(2):141-6). Some researchers compared oxidative stress levels in patients with dry eyes and those without dry eye in conjunctival epithelial cells in dry eye models and SS patients through tear test, fluorescein clearance, BUT scores and OSDI scores (Graefes Arch Clin Exp Ophthalmol. 2015 March; 253(3):425-30). Oxidative stress in patients with dry eyes was found to be higher than in those without dry eyes. In SS NOD (NOD.B10.Sn-H2) mouse model, pancreatic exocrine cells and artificially cultured human salivary gland cells, the antioxidant epigallocatechin has increased defensive antioxidant capacity through the mitogen-activated protein kinase signaling pathway (Autoimmunity. 2014 May; 47(3):177-84). The above documents all show that oxidative stress participates in the destruction of salivary gland tissue in SS and participates in the pathological process of SS.

Recent studies (Pagano et al., Free Radic Res. 2013 February; 47(2):71-3) have found that in plasma of SS patients, protein oxidation, myeloperoxidase activity, TNF-α, nitrotyrosine, and the level of glutathione changed significantly. In SS patients, changes in mitochondria of the cells and mitochondrial dysfunction result in the oxidative stress-related disorders, involving in the formation of oxidative stress.

In addition, it has been reported that thioredoxin (TRX) exerts a protective effect against salivary gland oxidative stress tissue damage in SS (J Rheumatol. 2007 October; 34(10):2035-43). In SS patients, a large amount of 8-OHdG and TRX were produced in salivary duct cells, and TRX was significantly negatively correlated with salivary flow rate. In addition, after acting on human salivary gland cells, TRX significantly inhibited IFN-γ-induced IL-6 expression and Fas-regulated apoptosis. TRX is an important antioxidant in cells, and even alone can eliminate the singlet oxygen and hydroxyl radicals. The expression of IL-6 and Fas-regulated apoptosis are the pathological process of typical inflammatory responses. Antioxidants inhibit the inflammatory response of inflammatory factors and apoptosis, thereby protecting the salivary glands of SS patients from tissue damage caused by inflammation. This also shows that oxidative stress can cause tissue damage by triggering the inflammatory response of the gland and thus participate in the pathogenesis of SS.

In summary, antioxidants can eliminate oxidative stress and inhibit the inflammatory damage caused by oxidative stress in the pathological process of SS, thereby preventing the pathological process of SS. Among others, the inflammatory injury process may be performed by activating the NF-κB pathway. Therefore, anti-oxidation may become a new SS treatment, and finding the right antioxidant may be an important direction for future research and development.

Common antioxidants are superoxide dismutase, catalase, thioredoxin, N-acetylcysteine, ergothioneine, vitamin C, vitamin D, vitamin E, glutathione, melatonin, alpha-lipoic acid, carotenoids, trace elements copper, zinc, selenium (Se) and so on.

Vitamin d has a wide range of effects, including inhibition of Th17 cell-mediated autoimmunity (Mol. Cell. Biol. 2011, 31(17):3653). Vitamin D deficiency (VitD) is common in SS patients, especially in female SS patients, which have a high risk of VitD deficiency (Erten et al., Int J Rheum Dis. 2015 January; 18(1):70-5). Low vitamin D levels in patients with SS may be associated with serious complications such as lymphoma and peripheral neuropathy. Supplementation of Vitamin D may be an additional tool for optimal treatment of SS. Vitamin D may play a role in pathological processes and disease expression of neuropathy in SS patients and may be used to monitor and treat this complication. There is a clear correlation between vitamin D deficiency and severe SS complications. It is recommended that vitamin D supplementation be given to every SS patient (BMC Med. 2013 Apr. 4; 11:93). However, vitamin D itself has no biological activity and needs to be further metabolized in the body to be hydroxylated into active vitamin D (1,25-Dihydroxyvitamin D3). Its clinical application dose is relatively large. In order to ensure efficacy, it is sometimes necessary to inject dosing.

N-acetylcysteine (NAC) is a precursor of glutathione synthesis in vivo and is an important antioxidant. In a study, 26 patients with primary or secondary Sjogren's syndrome are selected to undergo a randomized, double-blind trial. The experimental and control groups were treated with N-acetylcysteine (NAC) and placebo for 4 days, respectively. As a result, it was found that after treatment with NAC, the pain, sensation of the eyes, bad breath and daytime thirst are improved. This indicates that NAC has a true therapeutic effect on the ocular symptoms of SS patients and deserves further investigation (Walters et al., Scand J Rheumatol Suppl. 1986; 61:253-8). However, the clinical application of NAC has obvious deficiencies: NAC is not stable in vivo and requires a large dose to ensure efficacy. At the same time, NAC is an acidic substance that needs to be taken up to 1.2 grams per day in human trials (Altem Med Rev. 2000 October; 5(5):467-71), which dose may cause gastrointestinal symptoms in some patients. Moreover, according to the 2010 Pharmacopoeia of the People's Republic of China, NAC is a well-known TB drug and has many other adverse effects, including severe poisoning.

Therefore, it is necessary to find more stable, safe, efficient pharmaceutical active substances, or drug combinations for the treatment of Sjogren's syndrome.

SUMMARY

The technical problem to be solved by the present invention is the shortcomings of the above-mentioned existing methods and drugs for the treatment of SS. Take the the known drugs for the treatment of SS, i.e., VitD and NAC for example, the stability of them is not high, the pharmaceutical activity is single, and a large dose is needed to ensure efficacy, resulting in many adverse reactions and other issues.

Pyrroloquinoline quinone (PQQ), see formula (I) below:

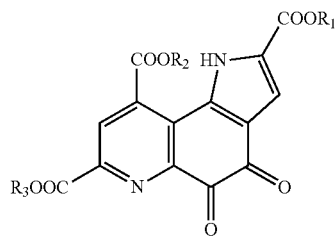

PQQ is a vicinal quinone compound containing three carboxylic acid groups. In the formula (I), R1, R2, and R3 are the same or different and each independently represents lower alkyl, lower alkenyl, lower alkynyl, aralkyl, alkaryl, phenyl, hydrogen, sodium, or potassium atom. The purified tricarboxylic acid form of PQQ is brick red with a molecular weight of 330.21. In 1979, the PQQ structure was confirmed. Since then its natural distribution, biosynthesis and biological functions have been extensively studied. PQQ is produced by certain gram-negative bacteria. Glutamate and tyrosine are the precursors of PQQ in the biosynthesis. Genes required for PQQ synthesis have also been cloned. PQQ is widely present in trace amounts of various microorganisms, plants and animals. PQQ is a water-soluble anionic complex that can act as an acceptor or donor of electrons involved in the enzymatic reaction of oxidoreductases. PQQ exists in the early stages of biogenesis and evolution. Many microorganisms can synthesize PQQ and play an important role in its own growth. Although there is controversy about whether PQQ is a novel vitamin (Bishop et al., Nutr Rev, 1998, 56(10): 287-93), it cannot be denied that PQQ exerts many important physiological functions in humans and animals. For example, PQQ can provide nutrition, prevent alcoholic liver damage, protect the heart from ischemia-reperfusion injury, scavenge free radicals, protect the body from free radical damage, increase the level of nerve growth factor in astrocytes, etc. (Matsushita et al. Appl Microbiol Biotechnol, 2002, 58(1): 13-22). Due to the unique o-quinone structure, PQQ has the physiological characteristics that other coenzymes do not have, and is relatively stable in terms of chemical properties. This feature enables it to participate in 20,000 redox cycles (Altem Med Rev. 2009 September; 14 (3): 268-77).

At present, the biological functions of PQQ are still in an exploratory stage. The main functions include: (1) stimulating the growth of microorganisms, plants, animals and human cells; (2) acting as an essential nutrient for animal growth, development and reproduction; (3) removing excessive free radicals and protecting the body from oxidative damage; (4) Providing neurotrophic and protective effects. Human experiments have shown that PQQ can improve sleep and cognition and reduce the expression of plasma inflammatory cytokines IL-6 and C-reactive protein (CRP). Some scholars have proposed to rank PQQ as the 14th vitamin in the B-vitamin category and have now been listed as a health product in the United States and Japan.

Through a large number of studies and experiments, the applicant surprisingly find that PQQ can significantly improve the salivary secretion function of NOD mice, which is the Sjogren's syndrome animal model. When PQQ is administrated in combination with active vitamin D, the improvement effect is more significant. In contrast, the same dose of active vitamin d used alone has no effect.

Through further research and experiments, the applicant also surprisingly find that: PQQ, PQQ combined with active vitamin D can significantly inhibit the oxidative stress levels and lymphocyte infiltration in submandibular gland tissues of NOD mice, significantly reduce the activity of an important inflammatory signaling pathway NF-kappaB signaling pathway, and significantly reduce the expression of cytokines such as Il-1, Il-6, and gamma interferon.

The aforementioned other antioxidants also include N-acetyl-L-cysteine, resveratrol, epigallocatechin gallate, curcumin, anthocyanins, tea polyphenols, vitamin B12, vitamin E, vitamins C or vitamin D.

The present invention provides novel pharmaceutical uses for pyrroloquinoline quinones, derivatives and/or salts thereof, and provides a pharmaceutical composition containing pyrroloquinoline quinone, derivatives and/or salts thereof as an active ingredient. The drugs containing pyrroloquinoline quinone, derivatives and/or salts thereof, or in combination with active VitD or NAC as an active ingredient, as compared to the drugs containing only active VitD or NAC as active ingredients, have the following advantages and progresses:

1) Stable. PQQ has a unique o-quinone structure and is relatively stable in chemical properties. This feature allows it to participate in 20,000 redox cycles, and its free radical scavenging activity is significantly higher than that of NAC or vitamin D;

2) Lower dosage. The amount of PQQ in rats used in this drug regimen is 1 mg per kilogram of body weight per day, which is much less than the amount of NAC used in animal experiments. 44-1300 mg per kilogram of body weight per day (*The American Journal of Pathology*, Vol. 175, No. 1, July 2009. Fertil Steril_2010; 94:2905-8.);

3) Safety. PQQ's rat LD50 was 1000-2000 mg/kg body weight, 100 mg/kg body weight per day for 14 consecutive days, no adverse reactions were found (Regul Toxicol Pharmacol. 2014 October; 70(1):107-21);

4) PQQ has a significant synergistic effect with active vitamin D, which greatly reduces the amount of active vitamin d and reduces the side effects of active vitamin d. The drug combination has a better prospect for the treatment of Sjogren's syndrome.

The use of pyrroloquinoline quinones, derivatives and/or salts thereof for the preparation of drugs for the treatment and/or prevention of Sjogren's syndrome, and the involvement of dry mouth, dry eyes and other exocrine glands and other organs outside the glands caused by Sjogren's syndrome with multiple systemic damages have not been reported at present. Moreover, its therapeutic effect on exocrine gland symptoms such as dry eyes and dry mouth in Sjogren's syndrome is better than that of VitD and NAC.

The first aspect of the present invention relates to use of Pyrroloquinoline quinones, derivatives and/or salts thereof in the preparation of drugs for the treatment and/or prevention of Sjogren's syndrome as well as dry mouth, dry eye and multiple system damages accompanied by the involvement of other exocrine glands and other organs outside the glands caused by Sjogren's syndrome;

A second aspect of the present invention relates to the use of the first aspect, wherein the Sjogren's syndrome comprises primary Sjogren's syndrome and secondary Sjogren's syndrome.

A third aspect of the present invention relates to the use of the first aspect, characterized in that the multiple system damages accompanied by the involvement of other organs outside the glands including chronic fatigue caused by Sjogren's syndrome.

A fourth aspect of the present invention relates to the use of the first aspect, characterized in that the pyrroloquinoline quinone, a derivative or a salt thereof is represented by the following structural formula (I):

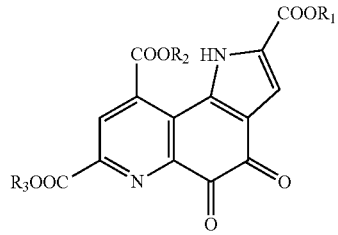

in formula (I), R1, R2 and R3 being same or different, each independently representing lower alkyl, lower alkenyl, lower alkynyl, aralkyl, alkaryl, phenyl, a hydrogen atom, sodium atom or a potassium atom.

A fifth aspect of the present invention relates to a pharmaceutical composition characterized by using a therapeutically and/or prophylactically effective amount of pyrroloquinoline quinone, a derivative thereof and/or a salt thereof in any one of the first to fourth aspects of the application as an active ingredient.

A sixth aspect of the present invention relates to a pharmaceutical composition according to the fifth aspect, characterized by further comprising active vitamin D (1,25-Dihydroxyvitamin D3).

A seventh aspect of the present invention relates to a pharmaceutical composition according to the fifth aspect, characterized in that the pyrroloquinoline quinone is in the tricarboxylic acid form.

An eighth aspect of the present invention relates to a pharmaceutical composition according to the fifth aspect, characterized in that the pyrroloquinoline quinone is in the form of a disodium salt.

A ninth aspect of the present invention relates to a pharmaceutical composition according to the fifth aspect, which is characterized by further comprising any one of the following substances or a mixture of any two or more of the following substances in any ratios: N-acetyl-L-cysteine, resveratrol, epigallocatechin gallate, curcumin, anthocyanins, tea polyphenols, vitamin B12, vitamin E, vitamin C or vitamin D.

DETAILED DESCRIPTIONS

Experimental Compound Sources and Treatments

Figure 1:
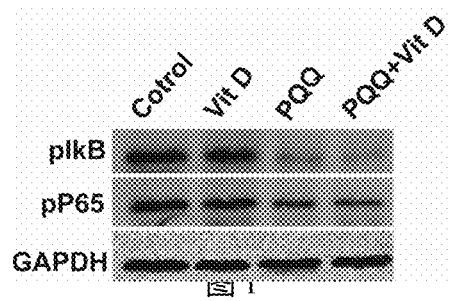
FIG. 1 shows the expression of NF-κB-related protein in different PQQ and active vitamin d treatment groups.
Figure 2:
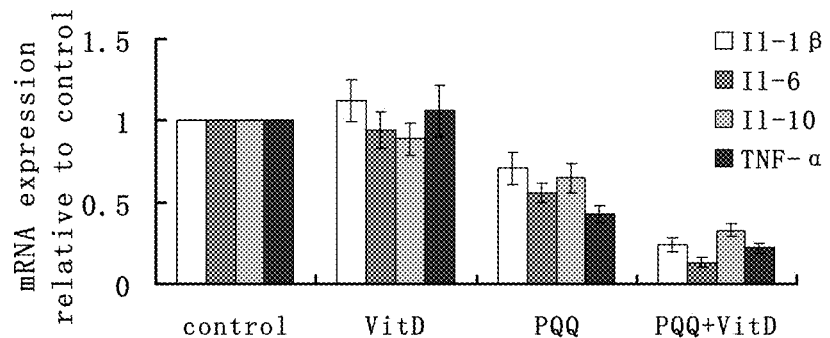
FIG. 2 shows that PQQ and active vitamin d synergistically inhibit the expression of inflammatory factors Il-1, Il-6, and gamma interferon.

PQQ (tricarboxylic acid form, pure), see Examples 1 to 5; Active Vitamin D (1,25-Dihydroxyvitamin D3), both purchased from Sigma Corporation, were dissolved in double distilled water, and the concentration of PQQ mother liquor was 1 mg/ml. The active vitamin d mother liquor concentration is 1 μg/ml. PQQ disodium salt form (PQQ-Na$_2$, donated by Mitsubishi Gas Chemical MGC, Japan), see Example VI, dissolved in water and the mother liquor concentration was 1 mg/ml.

Example I: PQQ Treats the Sjogren's Syndrome in Experimental Animals

Method:

Model: NOD mouse model. NOD (Non-obese Diabetes) mice are a genetically deficient animal model of spontaneous diabetes. The female mice develop diabetes from 14 weeks and the incidence can reach as high as 80% by 30 weeks. NOD mice are also an animal model of Sjogren's syndrome. Mice develop inflammatory cell infiltration in the submandibular gland from 12 weeks of age, with increased expression of multiple inflammatory factors, and reduced salivary secretion and increased salivary salt concentration from 16 to 20 weeks of age.

Experimental grouping: 8-week-old female NOD mice were purchased from Shanghai SLE Experimental Animal Corporation and divided into control group, active vitamin d group, PQQ group and PQQ combined with active vitamin D group. There were four different treatment groups, 10 in each group. Saliva flow rates were measured at 12, 24, and 36 weeks of age. The amounts of PQQ and active vitamin D were 1 mg/kg body weight per day and 0.1 μg/kg body weight per day, respectively.

Saliva Flow Detection:

a. Intraperitoneal injection of 1.2% avertin (Chinese name: tribromoethanol), injection dose: 0.2 ml/10 g body weight, formula: (1) 0.4 g avertin dissolved in 0.25 ml t-amyl alcohol, shaking for 12 hours to completely dissolve; (2) Add 19.75 ml of 0.9% NaCl solution to obtain 1.2% avertin. Mice were anesthetized gently.

b. Subcutaneous pilocarpine injection in the neck, injection dose: 0.5 mg/kg=0.01 mg/20 g body weight, mother liquor concentration: 0.5 g/10 ml physiological saline=50 mg/ml=0.05×10$^3$ mg/ml, solution concentration: the mother liquor was diluted 1000 times, ie, 0.05 mg/ml, to stimulate saliva secretion.

c. Began to collect saliva after 5 minutes, that is, cotton ball with about 8 mg dry weight is made from sterile cotton ball, which is then put into a 1.5 mL EP tube to determine the dry weight. When measuring saliva secretion, the cotton ball is put into the mouse cheek and then taken into the EP tube after 10 min. The wet weight is determined on the electronic balance. Saliva secretion=wet weight of cotton balls–dry weight of cotton balls.

Result:

At the age of 12 weeks of treatment, there was no significant difference in the salivary flow rate between the experimental groups and the control group. At the age of 24 weeks of treatment, the salivary flow was significantly increased in the PQQ+ active vitamin d group compared with the control group (P<0.05). However, there was no significant difference between the active vitamin D group and the PQQ group compared with the control group. At the age of 36th week of treatment, the PQQ+ active vitamin D group and the PQQ group were significantly higher than the control group, respectively. The difference was statistically significant (P<0.05). The PQQ+ active vitamin D group was more effective than the PQQ alone group (P<0.05). There was no statistical difference between the active vitamin d group and the control group. The above results fully demonstrate that PQQ can effectively relieve the symptoms of Sjogren's syndrome, but the use of small doses of active vitamin D alone has no therapeutic effect, indicating that the synergy between PQQ and active vitamin D is significant.

TABLE 1

Effect of PQQ and active vitamin D treatment on salivary flow (SFR) in mice

| Weeks of age | Control group SFR ($\mu$l/g/10 min) | active vitamin D group SFR ($\mu$l/g/10 min) | PQQ group SFR ($\mu$l/g/10 min) | PQQ+ active vitamin D group SFR ($\mu$l/g/10 min) |
|---|---|---|---|---|
| 12 W | 2.71 (n = 10) | 2.74 (n = 10) | 2.55 (n = 10) | 3.00 (n = 11) |
| 24 W | 2.76 (n = 6) | 2.82 (n = 5) | 3.21 (n = 6) | 3.51* (n = 6) |
| 36 W | 2.73 (n = 5) | 3.22 (n = 4) | 3.75* (n = 5) | 4.62* #(n = 4) |

Note:
*indicates that each group is compared with the control group, P < 0.05;
indicates that the PQQ+ active vitamin D group is compared with the PQQ group, P < 0.05

Example 2: PQQ Inhibits Activation of NF-κB

Method:

Detection of NF-κB Activation in Submandibular Gland Tissue of Mouse Submandibular Gland by Western Blot Take the same amount of total protein for each sample, add 4×SDS loading buffer according to the ratio of protein sample: 4×SDS at 3:1, mix well, boil at 95° C. for 5 min, and prepare 10% separation gel and 5% concentration gel. Perform SDS-PAGE electrophoresis, transfer the membrane, and block the PVDF membrane with 5% solution of skim milk in TBST for 1 hour at room temperature or overnight at 4° C. Dilute antibody with blocking solution, incubate at room temperature for 2 h or 4° C. overnight. Wash membrane, incubate with secondary antibody, and then wash the membrane again. After the equal volume of liquids A and B in the luminescence kit were mixed in a vessel, the mixture was uniformly added dropwise to the PVDF membrane, and the reaction was carried out in the dark for 3-5 minutes.

Result:

At the 36th week of treatment, the mouse submandibular glands were taken and Western Blot was used to detect the activation of NF-κB. It is indicated that there was no significant change in the Vit D group compared with the control group, but the phosphorylation level of P65 in the PQQ group and the PQQ+ active vitamin D group was significantly attenuated. P65 is the protein subunit of NF-κB, and its phosphorylation level directly reflects the activity of NF-κB. In addition, IκB binds to NF-κB to prevent its entry into the nucleus and exerts its activity. Once IκB is phosphorylated, it is degraded and releases NF-κB. Herein, the phosphorylation level of IκB in the PQQ group and the PQQ+ active vitamin d group was significantly attenuated, indicating that the activation level of NF-κB was significantly inhibited. See FIG. 1.

Example 3: PQQ and Active Vitamin d Synergistically Inhibit the Expression of Inflammatory Factors in Tissues Method:

Take the mouse submandibular gland tissue and extract RNA using Trizol. Superscript III was used for reverse transcription. Reaction was performed at 42° C. for 30 minutes. Oligo dT and Random Hexamer were used as primers for reverse transcription. Realtime quantitative PCR reaction system: 2×PCR premix 10 μl, Primers 0.8 μl, cDNA 1 μl, add balance of $H_2O$ to 20 μl; Reaction conditions: 95° C. 10 min, 95° C. 15 s, 60° C. 60 s, Read plate for 50 cycles; Melting curve Analysis: Temperature 55° C.-95° C., read once per minute. Set up 3 replicates for each sample.

Result:

Quantitative PCR technique was used to analyze the expression level of inflammatory factors in mouse submandibular glands tissue. It was found that PQQ treatment significantly inhibited the expression of IL-1β, IL-6, IL-10, and TNF-α (p<0.05) at 36 weeks. However, the use of active vitamin D alone did not detect the effect. While the combined use of PQQ and active vitamin d was more pronounced, and was significantly different from the treatment with PQQ alone (p<0.05).

Example 4: Oxygen Radical Detection

Method:

Detection of MDA content: The submandibular gland tissue in the submandibular glands of mice were harvested and homogenized with icy physiological saline. The protein content was quantified by BCA. Take 1 ml homogenate, add 1 ml 30% trichloroacetic acid and 1 ml 0.67% TBA in turn, bath in boiling water for 30 min and cool to room temperature. After centrifugation at 3000 g for 10 min, the absorbance (A) of the supernatant was measured at 535 nm, and the MDA content was calculated from the standard curve. The result was expressed in nmol/mg tissue.

Detection of SOD content: The submandibular gland tissue of mice were used to prepare tissue homogenates with icy physiological saline, and the protein content was quantified by BCA method. Refer to the kit operation instructions. Take 0.2 ml of the sample and mix it with 1.3 ml of test solution. Incubate at 37° C. for 40 min. Add 2 ml of chromogenic agent. Placed at room temperature for 10 min. Determine OD at 550 nm. The results are expressed in terms of U/mg protein, which states that the corresponding SOD amount per milligram of protein in a 1 ml reaction solution with a SOD inhibition rate of 50% is an SOD activity unit.

Result:

The involvement of oxygen radicals in lipid peroxidation reaction is an important factor in the inflammatory response. Oxygen radicals participate in lipid peroxidation and produce lipid peroxides, such as malondialdehyde (MDA). Lipid peroxidation reaction and the decomposition products of lipid peroxides can cause damage to the cell membrane structure and release a large number of inflammatory mediators. Lipid peroxide is also involved in the production of certain inflammatory mediators, such as the promotion of the synthesis of prostaglandin from arachidonic acid via the activation of cyclooxygenase. By measuring MDA that reflects the extent of lipid peroxides, indirect assessment of cell tissue damage can be made. SOD can effectively scavenge oxygen free radicals, thereby inhibiting lipid peroxidation in intestinal tissues and stabilizing cell membrane SOD activity. It is a major indicator of cell membrane function and anti-inflammatory response of the body.

The results showed that when treated with PQQ alone for 36 weeks, compared with the control group, the content of MDA was significantly lower (P<0.05) and the content of SOD was significantly higher than that of the control group. When treated with Vit D alone, there was no significant difference. When treated with PQQ+Vit D, compared with the control group, the contents of MDA and SOD were significantly changed, and there was significant synergy (P<0.05). It is fully demonstrated that PQQ can effectively inhibit oxygen radicals caused lipid peroxidation and protect cells from oxygen radical damage sufficiently and synergistically in combination with Vit D.

TABLE 2

Effect of treatment with PQQ and active vitamin d on MDA and SOD in submandibular gland tissue of mice at 36 weeks of age

| Groups | MDA (Mean ± SD, nmol/mg protein) | SOD (Mean ± SD, NU/mg protein) |
| --- | --- | --- |
| Control group | 9.92 ± 1.35 | 110.87 ± 15.62 |
| Vit D group | 9.48 ± 2.12 | 102.45 ± 14.22 |
| PQQ group | 4.61 ± 0.76* | 198.21 ± 21.33* |
| PQQ+Vit D group | 3.12 ± 0.34*# | 235.55 ± 2.8.11*# |

Note:
*indicates that each group is compared with the control group, P < 0.05;
indicates that the PQQ+ active vitamin D group is compared with the PQQ group, P < 0.05

Example 5: Mouse Submandibular Gland Tissue Slice Detection

Method:
36 weeks age of mouse submandibular gland tissue was isolated, embedded in paraffin and sliced, stained with hematoxylin-eosin and photographed with an inverted microscope.

Figure 3:
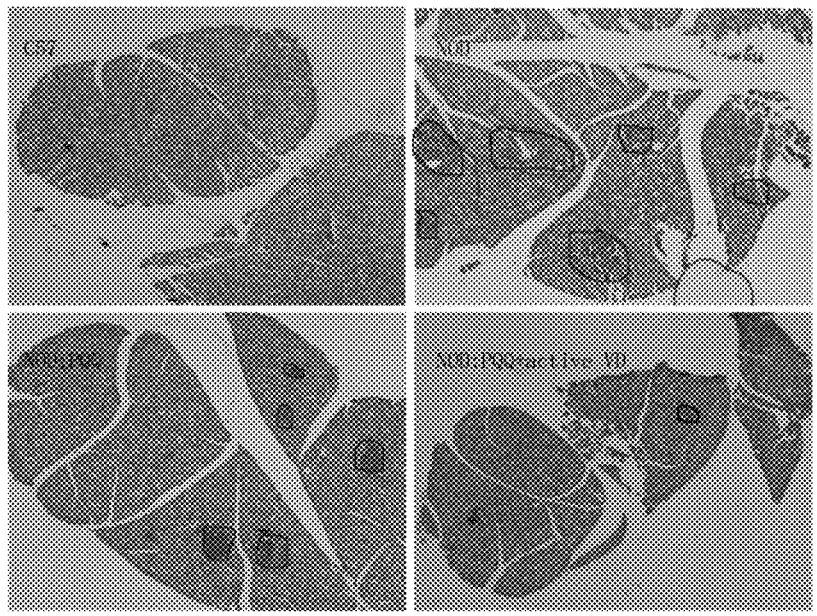
FIG. 3 shows the effect of PQQ and active vitamin d treatment on lymphocytic infiltration in mouse submandibular glands.

Result:
Lymphocytic infiltration in the gland showed clumps, as shown in FIG. 3. Normal C57 mice showed no Sjogren symptoms, no lymphocyte clump infiltration. NOD mice showed submandibular lymphocytes infiltration, while the area of infiltration of lymphocytes in PQQ treatment group was significantly reduced. PQQ combined with active vitamin D group, compared with PQQ group, the area of lymphocyte infiltration was further reduced.

Example 6: The Treatment and Prevention of Sjogren's Syndrome in Experimental Animals with PQQ Materials and Methods:
In this experiment, the methods were the same as in Example 1 except that the PQQ disodium salt form (PQQ-Na$_2$) was used, and the administration time was 24 weeks.

Figure 4:
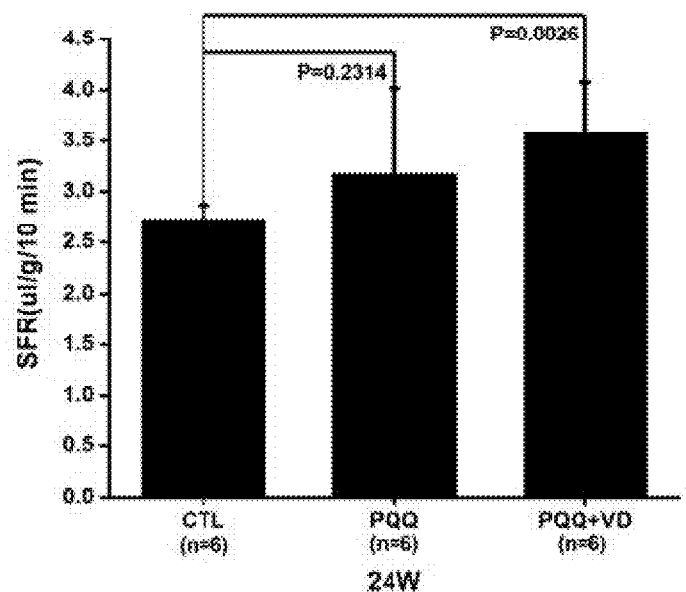
FIG. 4 shows the effect of PQQ and active vitamin D treatment on salivary flow (SFR) in mice.
Figure 5:
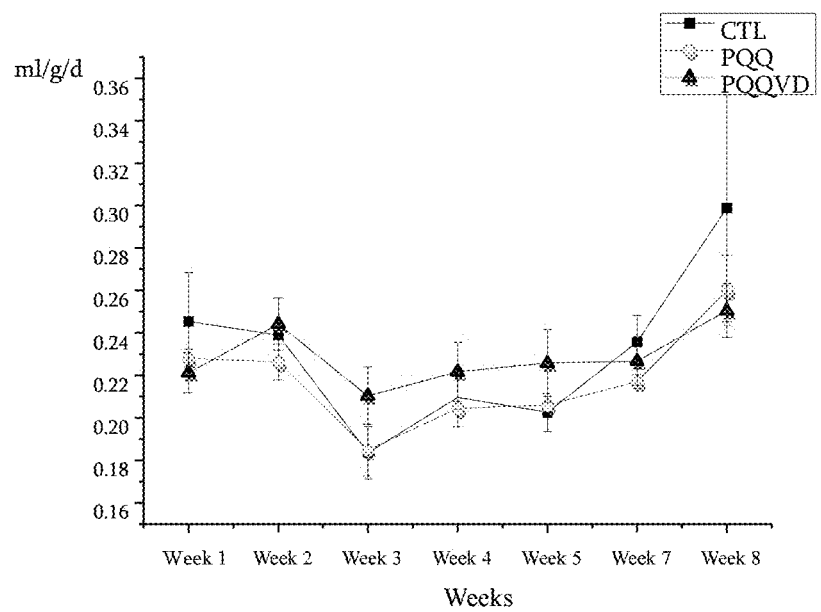
FIG. 5 shows the amount of drinking water in the first 8 weeks of treatment with PQQ and active vitamin D-treated mice.

After administration, the weekly drinking water of the mice per cage was measured. The weekly drinking water was measured and converted into milliliters of water per gram of body weight. The results suggest that from the 8th week, the drinking water of the control group of mice was significantly increased compared with that of the medication group. The onset of Sjogren's syndrome began in the eighth week of the control group, while the medication group was normal. See FIG. 4 and FIG. 5.

Dosage and Dosage Forms

Dose of PQQ:
In the present invention, the dose of PQQ used in animal experiment is 1 mg/kg/day. This dose is commonly used in animal experiments, corresponding to about 60 mg/day for adults. Taking into account the difference in metabolic rates between humans and mice, this dose is approximately 10 mg/per day for adults (The assumed adult body weight was 60 kg, the same as below).

Dose of active vitamin D: 0.1 μg/kg/day, corresponding to approximately 0.6 μg/day for adults. This is a safe dose that the body can tolerate.

The above drugs are all oral dosage forms, that is, formulated as aqueous solutions and mixed into the drinking water. The amount of the drugs can be fine-tuned according to the daily drinking water of mice. Those skilled in the art can determine suitable dose range and suitable oral dosage form through limited experiments without any creative labor according to the disclosure of the present application. Therefore, any dose range and suitable oral dosage form suitable for the purpose of the present invention also fall into the range within the scope of the present invention.

What is claimed is:

1. A method of treating Sjögren's syndrome, comprising: administering to a subject exhibiting Sjögren's syndrome, dry mouth, or dry eye, a pharmaceutically effective amount of pyrroloquinoline quinone, and/or a salt thereof.

2. The method of claim 1, characterized in that said Sjögren's syndrome includes primary Sjögren's syndrome and secondary Sjögren's syndrome.

3. The method according to claim 1, wherein the pyrroloquinoline quinone and/or salt thereof is administered to the subject in an amount of 1 mg/kg body weight per day.

4. The method of claim 1, further comprising administering to the subject active vitamin D (1,25-Dihydroxyvitamin D3).

5. The method according to claim 4, wherein active vitamin D and pyrroloquinoline quinone and/or salt thereof is administered to the subject in an amount of 1 mg/kg body weight per day and 0.1 μg/kg body weight per day, respectively.

6. The method according to claim 1, wherein the pyrroloquinoline quinone salt is a disodium salt of pyrroloquinoline quinone.

7. The method according to claim 1, wherein the subject is concurrently administered any one or more of the following substances: N-acetyl-L-cysteine, resveratrol, Epigallocatechin gallate, curcumin, anthocyanins, tea polyphenols, vitamin B12, vitamin E, vitamin C, and vitamin D.

8. A method of treating Sjögren's syndrome, which consists of administering to a subject exhibiting Sjögren's syndrome, dry mouth, or dry eye, a composition consisting of a combination of: (a) pyrroloquinoline quinone, and/or a salt thereof, in an amount of 1 mg/kg body weight per day, and (b) 1,25-dihydroxyvitamin D3 (vitamin D) in an amount of 0.1 μg/kg/day.

* * * * *